United States Patent
Schuler et al.

(10) Patent No.: US 7,905,230 B2
(45) Date of Patent: Mar. 15, 2011

(54) METERED DOSE INHALER WITH LOCKOUT

(75) Inventors: Carlos A. Schuler, Cupertino, CA (US); William Alston, San Jose, CA (US)

(73) Assignee: Novartis AG, Basel (CH)

( * ) Notice: Subject to any disclaimer, the term of this patent is extended or adjusted under 35 U.S.C. 154(b) by 1753 days.

(21) Appl. No.: 10/734,076

(22) Filed: Dec. 10, 2003

(65) Prior Publication Data
US 2005/0056276 A1   Mar. 17, 2005

Related U.S. Application Data

(63) Continuation-in-part of application No. 09/852,408, filed on May 9, 2001.

(60) Provisional application No. 60/436,807, filed on Dec. 27, 2002.

(51) Int. Cl.
*A61M 11/00* (2006.01)
*A61M 15/00* (2006.01)
*A61M 16/00* (2006.01)
*A61M 15/08* (2006.01)

(52) U.S. Cl. .......... 128/200.23; 128/200.14; 128/200.16; 128/200.18; 128/203.12; 128/203.15; 128/203.23; 128/203.19; 128/202.21

(58) Field of Classification Search ............. 128/203.19, 128/200.23, 203.23, 202.21, 203.12, 203.15, 128/200.14, 200.16, 200.18
See application file for complete search history.

(56) References Cited

U.S. PATENT DOCUMENTS

| | | | |
|---|---|---|---|
| 3,636,949 A * | 1/1972 | Kropp | 128/200.23 |
| 4,677,975 A | 7/1987 | Edgar et al. | |
| 4,934,358 A | 6/1990 | Nilsson et al. | |
| 4,955,371 A | 9/1990 | Zamba et al. | |
| 4,984,158 A | 1/1991 | Hillsman | |
| 5,118,494 A | 6/1992 | Schultz et al. | |
| 5,215,079 A | 6/1993 | Fine et al. | |
| 5,284,133 A | 2/1994 | Burns et al. | |
| 5,392,768 A | 2/1995 | Johansson et al. | |
| 5,458,135 A | 10/1995 | Patton et al. | |
| 5,492,688 A | 2/1996 | Byron et al. | |
| 5,497,764 A | 3/1996 | Ritson et al. | |

(Continued)

FOREIGN PATENT DOCUMENTS

DE   28 09 255   3/1978

(Continued)

OTHER PUBLICATIONS

S.P. Newman, "Deposition and Effects of Inhalation Aerosols", (1983), London, GB; pp. 23-30.

*Primary Examiner* — Tatyana Zalukaeva
*Assistant Examiner* — Nihir Patel
(74) *Attorney, Agent, or Firm* — Janah & Associates, PC

(57) ABSTRACT

An aerosolization device comprises a housing, a container comprising a reservoir storing a pharmaceutical formulation which comprises a propellant, and a metering valve. The metering valve is in communication with the reservoir and is moveable into the container to an actuated position where a predetermined amount of the pharmaceutical formulation is released. A contact member is provided in the housing. In one version, the contact member is moveable between a first position and a second position to allow for selective actuation of the metering valve. In another version, the contact member's configuration may be changed to allow for selective actuation of the metering valve.

32 Claims, 5 Drawing Sheets

U.S. PATENT DOCUMENTS

| | | |
|---|---|---|
| 5,507,277 A | 4/1996 | Rubsamen et al. |
| 5,605,674 A | 2/1997 | Purewal et al. |
| 5,655,520 A | 8/1997 | Howe et al. |
| 5,683,677 A | 11/1997 | Purewal et al. |
| 5,692,492 A | 12/1997 | Bruna et al. |
| 5,694,919 A | 12/1997 | Rubsamen et al. |
| 5,724,957 A | 3/1998 | Rubsamen et al. |
| 5,735,263 A | 4/1998 | Rubsamen et al. |
| 5,740,794 A | 4/1998 | Smith et al. |
| 5,775,320 A | 7/1998 | Patton et al. |
| 5,785,049 A | 7/1998 | Smith et al. |
| 5,833,066 A | 11/1998 | Hargus et al. |
| 5,910,301 A | 6/1999 | Farr et al. |
| 5,915,378 A | 6/1999 | Lloyd et al. |
| 5,922,675 A | 7/1999 | Baker et al. |
| 6,029,661 A | 2/2000 | Whaley et al. |
| 6,089,228 A | 7/2000 | Smith et al. |
| 6,142,339 A | 11/2000 | Blacker et al. |
| 6,234,366 B1 | 5/2001 | Fuchs |
| 6,257,233 B1 | 7/2001 | Burr et al. |
| 6,260,549 B1 | 7/2001 | Sosiak |
| 6,273,084 B1 | 8/2001 | Frid |
| 6,309,623 B1 | 10/2001 | Weers et al. |
| 6,606,992 B1 | 8/2003 | Schuler et al. |

FOREIGN PATENT DOCUMENTS

| | | |
|---|---|---|
| GB | 2 191 718 | 12/1987 |
| WO | 91/04011 | 4/1991 |
| WO | 91/11173 | 8/1991 |
| WO | 92/00107 | 1/1992 |
| WO | 92/07599 | 5/1992 |
| WO | WO 92/07599 * | 5/1992 |
| WO | 94/16759 | 8/1994 |
| WO | 95/17195 | 6/1995 |
| WO | 95/24183 | 9/1995 |
| WO | 96/32096 | 10/1996 |
| WO | 96/32149 | 10/1996 |
| WO | 97/12639 | 4/1997 |
| WO | 99/16419 | 4/1999 |
| WO | 99/16422 | 4/1999 |
| WO | 00/24362 | 5/2000 |
| WO | 00/72904 | 12/2000 |
| WO | 01/00263 | 1/2001 |
| WO | 01/93932 | 12/2001 |

* cited by examiner

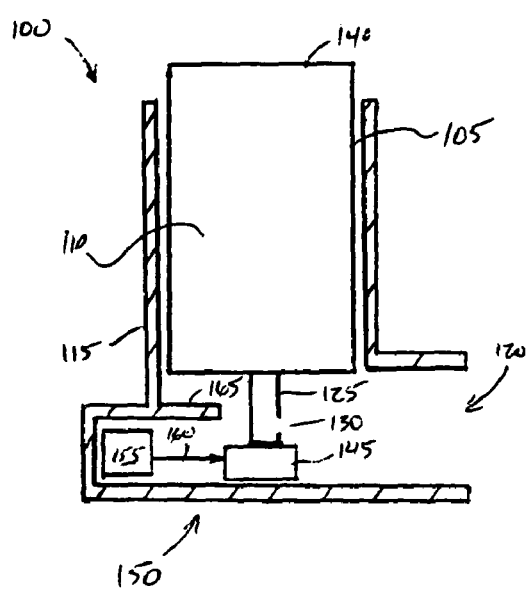
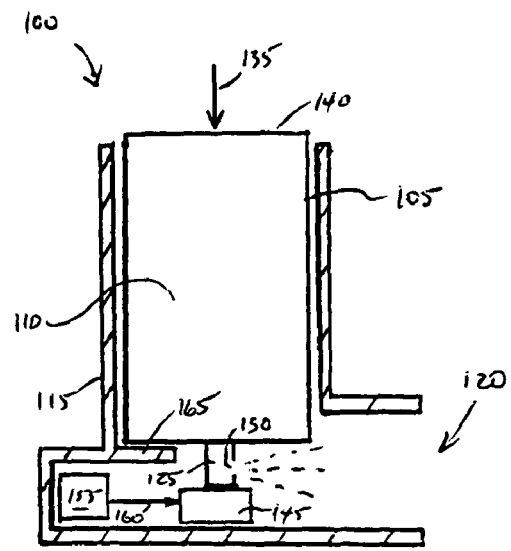
Figure 1A
Figure 1B
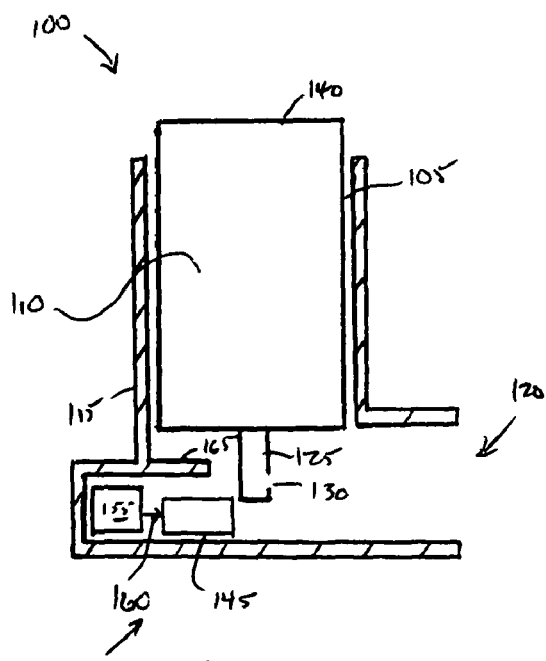
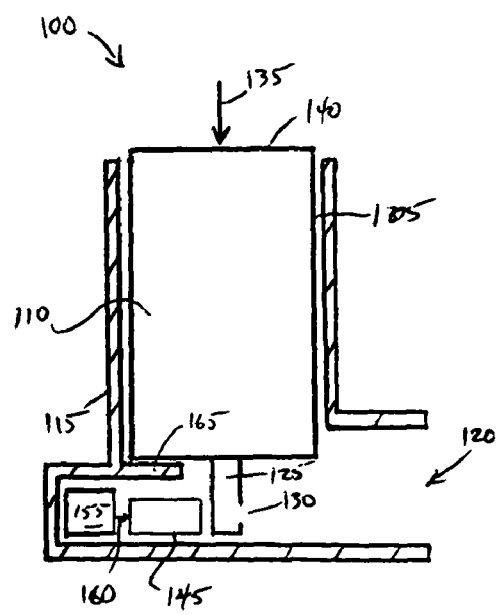
Figure 2A
Figure 2B

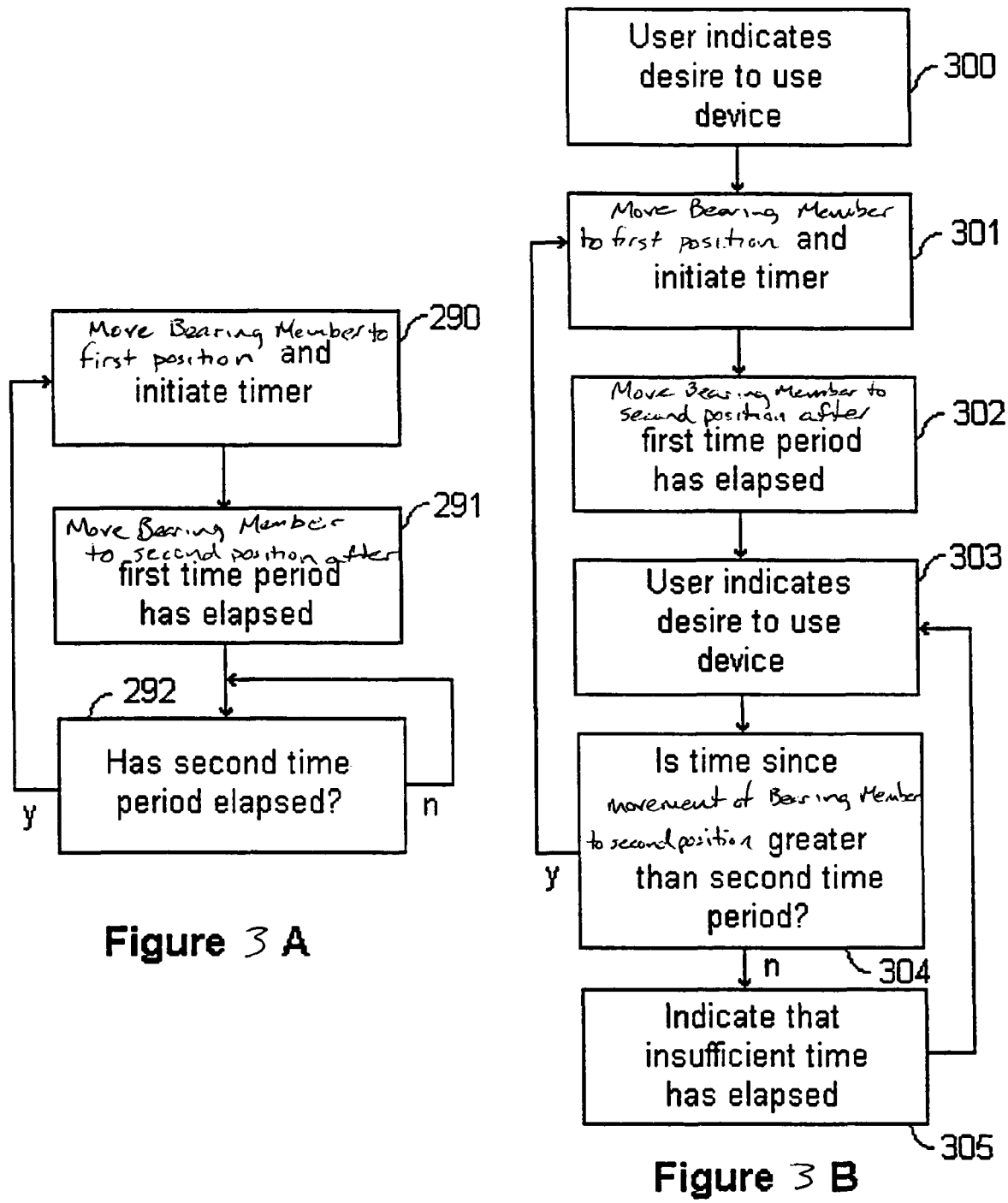

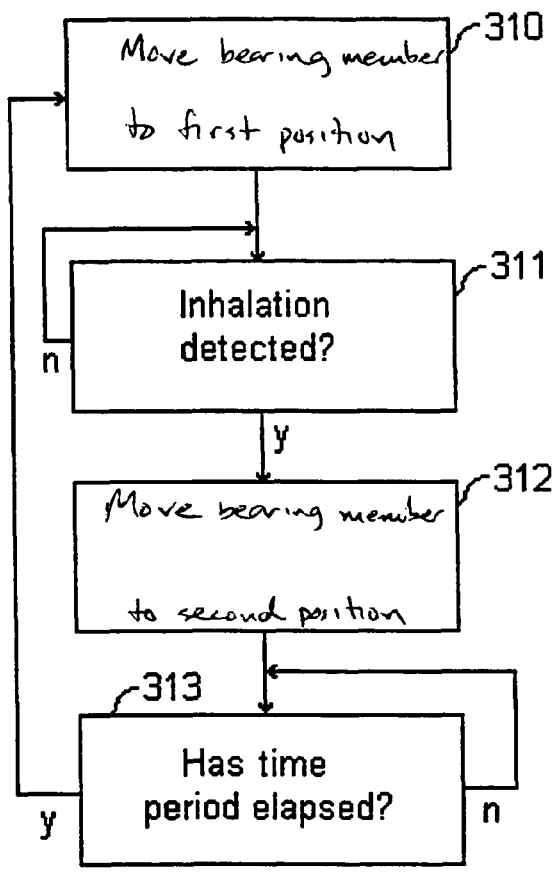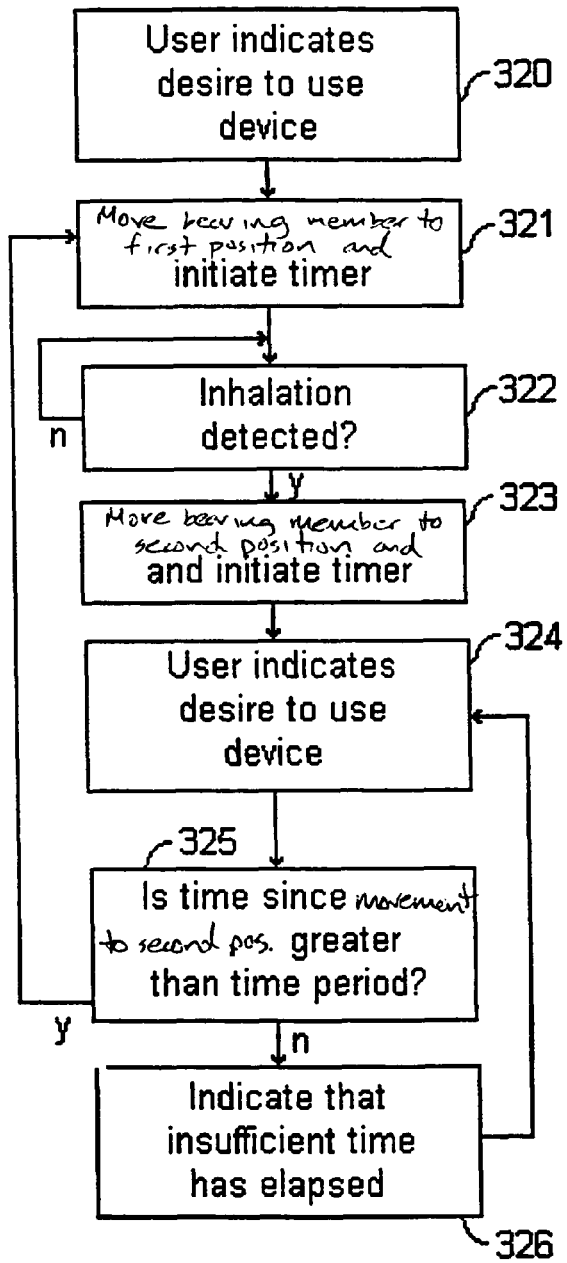
Figure 4 A
Figure 4 B

```
┌─────────────────┐
│ User engages    │
│ mouthpiece and  │──── 330
│ inhales         │
└────────┬────────┘
         ▼
┌─────────────────┐
│ Sense pressure  │──── 331
│ in airway       │◄─────────┐
└────────┬────────┘          │
         ▼                   │
┌─────────────────┐          │
│ Is pressure less│──── 332  │
│ than threshold  │          │
│ pressure?       │          │
└──n──────────y───┘          │
   │          │              │
   │          ▼              │
   │  ┌──────────────┐       │
   │  │ Move bearing │──333  │
   │  │ member to    │       │
   │  │ first position│      │
   │  └──────┬───────┘       │
   │         ▼               │
   │  ┌──────────────┐       │
   │  │ Aerosolize   │──335  │
   │  │ pharmaceutical│      │
   │  │ formulation  │       │
   │  └──────┬───────┘       │
   │         ▼               │
   │  ┌──────────────┐       │
   │  │ Deliver      │──336  │
   │  │ aerosolized  │       │
   │  │ pharmaceutical│      │
   │  │ formulation to lungs│
   │  └──────────────┘       │
   │                         │
   ▼                         │
┌──────────────┐             │
│ User continues│── 334      │
│ inhaling      │────────────┘
└──────────────┘
```

Figure 5

METERED DOSE INHALER WITH LOCKOUT

This application is a continuation in part of U.S. patent application Ser. No. 09/852,408 filed on May 9, 2001, which is incorporated herein by reference in its entirety and this application claims the benefit of U.S. Provisional Patent Application Ser. No. 60/436,807 filed on Dec. 27, 2002.

BACKGROUND

The need for effective therapeutic treatment of patients has resulted in the development of a variety of pharmaceutical formulation delivery techniques. One traditional technique involves the oral delivery of a pharmaceutical formulation in the form of a pill, capsule, elixir, or the like. However, oral delivery can in some cases be undesirable. For example, many pharmaceutical formulations may be degraded in the digestive tract before they can be effectively absorbed by the body. Inhaleable drug delivery, where an aerosolized pharmaceutical formulation is orally or nasally inhaled by a patient to deliver the formulation to the patient's respiratory tract, has proven to be a particularly effective and/or desirable alternative. For example, in one inhalation technique, an aerosolized pharmaceutical formulation provides local therapeutic relief to a portion of the respiratory tract, such as the lungs, to treat diseases such as asthma and emphysema. In another inhalation technique, a pharmaceutical formulation is delivered deep within a patient's lungs where it may be absorbed into the blood stream. Many types of aerosolization devices exist including devices comprising a pharmaceutical formulation stored in or with a propellant, devices that aerosolize a dry powder, devices which use a compressed gas to aerosolize a liquid pharmaceutical formulation, and similar devices.

One conventional type of aerosolization device is commonly referred to as a metered dose inhaler (MDI), which are sometimes referred to as a pressurized metered dose inhaler (pMDI). In a metered dose inhaler, a pharmaceutical formulation and a propellant are stored in a container, such as a canister. In one version the pharmaceutical formulation is suspended within the propellant, and in another version the pharmaceutical formulation is dissolved in the propellant. In either version, a valve may be actuated so that a metered amount, such as a dose or a portion of a dose, of the pharmaceutical formulation is aerosolized in a manner where is may be inhaled by a user. The canister may contain one or more doses of the pharmaceutical formulation and generally contains sufficient amounts of propellant to allow for several actuations. Traditionally, the propellant comprises one or more chlorofluorocarbon compounds. However, non-chlorinated propellants, such as hydrofluoroalkanes, that are believed to be more environmentally friendly are proving to be a desirable alternative.

Though generally well accepted and inexpensive, conventional metered does inhalers have certain drawbacks. For example, the operation of the metered dose inhaler is generally not controllable. Accordingly, any person at any time may actuate the metered dose inhaler aerosolizing the pharmaceutical formulation.

Therefore, it is desirable to be able to control the operation of a metered dose inhaler. It is further desirable to be able to control the operation of the metered dose inhaler in a simple and easily manufacturable, and unencumbering manner.

SUMMARY

The present invention satisfies these needs. In one aspect of the invention, the actuation of an MDI is prevented in a manner other than by preventing movement of the cannister.

In another aspect of the invention, an aerosolization device comprises a housing; a container comprising a reservoir storing a pharmaceutical formulation which comprises a propellant; a metering valve in communication with the reservoir, the metering valve being moveable into the container to an actuated position, wherein a predetermined amount of the pharmaceutical formulation is released when the metering valve is moved to the actuated position; and a contact member in the housing, the contact member being moveable between a first position and a second position, wherein a portion of the metering valve is able to contact the contact member when in the first position and is unable to contact the contact member when in the second position.

In another aspect of the invention, an aerosolization device comprises a housing; a container comprising a reservoir storing a pharmaceutical formulation which comprises a propellant; a metering valve in communication with the reservoir, the metering valve being moveable into the container to an actuated position, wherein a predetermined amount of the pharmaceutical formulation is released when the metering valve is moved to the actuated position; and a contact member in the housing, the contact member having a first configuration and a second configuration, wherein a portion of the metering valve is able to contact the contact member when in the first configuration in a manner which allows the metering valve to be moved to the actuated position.

In another aspect of the invention, an aerosolization device comprises a housing; a container comprising a reservoir storing a pharmaceutical formulation which comprises a propellant; a metering valve in communication with the reservoir, the metering valve being moveable into the container to an actuated position, wherein a predetermined amount of the pharmaceutical formulation is released when the metering valve is moved to the actuated position; and a contact member in the housing, the contact member being moveable from a first condition to a second condition, wherein when the contact member is in the first condition, the metering valve may contact the contact member so as to allow the metering valve to be moved to the actuated position.

In another aspect of the invention, an aerosolization device comprises a housing; a container comprising a reservoir storing a pharmaceutical formulation which comprises a propellant; a metering valve in communication with the reservoir, the metering valve being moveable into the container to an actuated position, wherein a predetermined amount of the pharmaceutical formulation is released when the metering valve is moved to the actuated position; and a contact member in the housing, wherein the metering valve may be moved to the actuated position when the metering valve and/or the container is able to contact the contact member and may not be actuated with the metering valve and/or the container is unable to contact the contact member.

In another aspect of the invention, an aerosolization device comprises a housing; a container comprising a reservoir storing a pharmaceutical formulation which comprises a propellant; a metering valve in communication with the reservoir, the metering valve being moveable into the container to an actuated position, wherein a predetermined amount of the pharmaceutical formulation is released when the metering valve is moved to the actuated position; and a contact member in the housing, wherein the metering valve may be moved to the actuated position when the metering valve and/or the container is able to contact the contact member in a rigid configuration and may not be actuated with the metering valve and/or the container is unable to contact the contact member in a rigid configuration.

In another aspect of the invention, a method of controlling the operation of an aerosolization device is provided, the aerosolization device comprising a container comprising a reservoir storing a pharmaceutical formulation which comprises a propellant, and the aerosolization device comprising a metering valve in communication with the reservoir, the metering valve being moveable into the container to an actuated position, wherein a predetermined amount of the pharmaceutical formulation is released when the metering valve is moved to the actuated position, The method comprises positioning a contact member in a first position where the contact member may contact the metering valve and/or the container to allow the metering valve to be moved to the actuated position; and positioning the contact member in a second position where the metering valve may not be moved to the actuated position.

In another aspect of the invention, a method of controlling the operation of an aerosolization device is provided, the aerosolization device comprising a container comprising a reservoir storing a pharmaceutical formulation which comprises a propellant, and the aerosolization device comprising a metering valve in communication with the reservoir, the metering valve being moveable into the container to an actuated position, wherein a predetermined amount of the pharmaceutical formulation is released when the metering valve is moved to the actuated position. The method comprises configuring a contact member in a first configuration wherein the contact member may contact the metering valve and/or the container to allow the metering valve to be moved to the actuated position; and configuring the contact member in a second configuration wherein the metering valve may not be moved to the actuated position.

DRAWINGS

These features, aspects, and advantages of the present invention will become better understood with regard to the following description, appended claims, and accompanying drawings which illustrate exemplary features of the invention. However, it is to be understood that each of the features can be used in the invention in general, not merely in the context of the particular drawings, and the invention includes any combination of these features, where:

FIG. 1A is a schematic sectional side view of an aerosolization device of the invention;

FIG. 1B is a schematic sectional side view of the aerosolization device of FIG. 1A during aerosolization;

FIG. 2A is a schematic sectional side view of the aerosolization device of FIGS. 1A and 1B in an unactuatable condition;

FIG. 2B is a schematic sectional side view of the aerosolization device of FIGS. 1A and 1B in an unactuatable condition during attempted aerosolization;

FIG. 3A is a flow chart illustrating a version of a control routine for an aerosolization device according to the invention;

FIG. 3B is a flow chart illustrating another version of a control routine for an aerosolization device according to the invention;

FIG. 4A is a flow chart illustrating another version of a control routine for an aerosolization device according to the invention;

FIG. 4B is a flow chart illustrating another version of a control routine for an aerosolization device according to the invention;

FIG. 5 is a flow chart illustrating another version of a control routine for an aerosolization device according to the invention.

DESCRIPTION

Figure 6A:
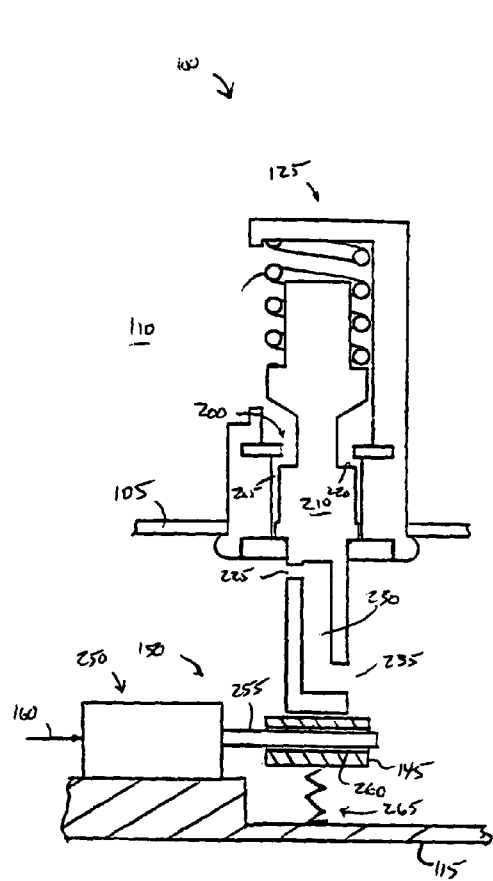
FIGS. 6A and 6B are schematic sectional side views showing the operation of another version of an aerosolization device according to invention.

The present invention relates to an aerosolization device, such as device that uses a propellant for aerosolization. Although the process is illustrated in the context of aerosolizing a predetermined amount of a pharmaceutical formulation, the present invention can be used in other processes and should not be limited to the examples provided herein.

An aerosolization device 100 of the present invention is shown schematically in FIG. 1A. A container 105 includes a reservoir 110 which stores a formulation, such as a pharmaceutical formulation, comprising a propellant. The pharmaceutical formulation may further comprise an active agent dissolved in or suspended in the propellant or a mixture comprising the propellant. The propellant may comprise a superheated liquid that may be used as an atomizing power source during actuation of the aerosolization device 100. As shown in FIG. 1A, the container 105 is housed within a housing 115 that includes a mouthpiece portion 120 though which a user may place his or her mouth, or nose, and inhale. The pharmaceutical formulation within the container 105 often includes a liquid portion and a gaseous portion also known as a headspace.

In communication with the reservoir 110 is a metering valve 125 that is capable of allowing a metered amount of the pharmaceutical formulation to be released from the reservoir 110 in an aerosolized form. The operation of the metering valve 125 is shown in FIGS. 1A and 1B. When the metering valve 125 is moved from an extended position, as shown in FIG. 1A, to a retracted position where the metering valve 125 is retracted into the container 105, a metered amount of the pharmaceutical formulation is ejected from an opening 130 in the metering valve 125 and is aerosolized so that the aerosolized pharmaceutical formulation may be inhaled by a user inhaling through the mouthpiece 120.

The aerosolization apparatus 100 may be actuated by a user. For example, as shown in FIG. 1B, a user may apply a force 135 to a top surface 140 of the container 105, or to an intermediate member, to cause the container 105 to move within the housing 115. As the container 105 moves within the housing 115, the metering valve 125 contacts a contact member 145 and the metering valve 125 is forced into the container 105, thereby actuating the aerosolization apparatus and causing a metered amount of the pharmaceutical formulation to be aerosolized.

The aerosolization apparatus 100 also comprises an actuation controlling mechanism 150. The actuation controlling mechanism 150 comprises a controller 155 that is in communication 160 with the contact member 145. The controller 150 is capable of controlling the position, condition, and/or the shape of the contact member 145 in accordance with a predetermined regimen. In one version, the contact member is moveable from a first position, as shown in FIGS. 1A and 1B, to a second position, as shown in FIGS. 2A and 2B and/or is moveable from the second position to the first position. As can be seen from the figures, when the contact member 145 is in the first position, it is located at a position where the metering valve 125 may bear against it when the force 135 is applied. In the second position, the contact member is located in a position where the metering valve does not bear against during movement of the container 105. Accordingly, when the contact member is in the second position, the aerosolization device 100 cannot be actuated since there is nothing to force the metering valve 125 into the container 105 to eject the metered dose of the pharmaceutical formulation. In one version, an abutment 165 is provided in or on the housing 115 to limit the travel of the container 105 within the housing 115.

In one version, the controller 155 maintains the contact member 145 in either the first position or the second position. For example, the controller 155 may maintain the contact member 145 in the second position in order to prevent unauthorized use of the aerosolization device 100. This may be desirable to prevent a user who is not a prescribed user of a pharmaceutical formulation from inhaling the formulation. To use the device, an authorized user may interact with the controller 155 through an input device in communication with the controller 155 to cause the controller 155 to move the contact member 145 from the second position to the first position. For example, the input device may comprise an array of number keys and the user may enter a code that informs the controller 155 that the user is authorized. Alternatively, a bar code reader or other recognition system, such as a system that recognizes a user's fingerprint or the like, may be used to communicate authorization to the controller 155.

In another version, the controller 155 may move the contact member to the first position in response to a detected condition, such as time. Some medicaments may be highly addictive and/or toxic when delivered to a user too frequently. Accordingly, it may be desirable to limit the delivery of the medicament beyond a prescribed amount, as described in U.S. patent application Ser. No. 09/852,408, filed on May 9, 2001 and entitled "Lockout Mechanism for Aerosol Drug Delivery", which is incorporated herein by reference in its entirety. Thus, in one version, the controller 155 includes or is in communication with a clock, and the controller 155 controls the positioning of the contact member 145 in accordance with a predetermined or programmed time scheme. Accordingly, the contact member 145 may be maintained at its second position until a signal is received from the controller 155 causing it to move to the first position to allow for the aerosolization apparatus 100 to be actuated.

Flow charts illustrating versions of time-control routines for an aerosolization device are shown in FIGS. 3A and 3B. In FIG. 3A, the contact member 145 is moved to the first position and a timer is initiated, as shown in step 290. The controller 155 then causes the contact member 145 to move to the second position after a first predetermined period of time has elapsed 291 since the movement of the contact member 145 to the first position. The first predetermined period is preferably sufficiently long to allow the user to unhurriedly use the aerosolization device 100 and sufficiently short to prevent multiple uses of the aerosolization device 100. For example, the first period may be for a period of from about 5 seconds to about 3 minutes, more preferably for a period of from about 20 seconds to about 1 minute, and most preferably for a period of about 30 seconds. Then, after a second predetermined time period has elapsed 292, the contact member 145 is again moved to the first position and the timer is reinitiated 290. Optionally, a signal, such as an audible, visual, or tactile indication, may be provided to inform the user that the aerosolization apparatus is actuateable. In the version of FIG. 3B, the input device is used by the patient to inform the controller 155 that the user desires medication 300. In response to an initial indication from the input device, the controller 155 causes the contact member 145 to move to the first position and initiates a timer 301. As in step 291, the contact member 145 is moved to the second position after a first predetermined time has elapsed 302. Later, the user uses the input device to indicate that medication is again desired 303. In response to step 303, the controller 155 assesses if at least the second predetermined time period has elapsed 304. If so, the contact member 145 is again moved to the first position, allowing the apparatus to be actuated, and the process repeats. If the second predetermined time period has not elapsed, an indication is provided 305 to the user that insufficient time has elapsed for use of the aerosolization apparatus 100. For example, an audible or tactile alarm or a display screen may be provided. The second predetermined time period may be a period sufficiently long to prevent over medication, and may be dependent on the pharmaceutical formulation and/or on the user. In one version, the second time period may be programmed into the controller 155 by a physician or a pharmacist when the aerosolization device is given to the patient. For example, the second predetermined time period may be 2 hours, 4, hours, 6 hours, 8, hours, 24 hours, etc. The first predetermined time period may also be selectable. In another version, the movement of the contact member 145 from the second position to the first position may be correlated with a particular time of day. Optionally, an output device, such as an audible or vibratory alarm, may be provided to inform the user when the aerosolization device is available to be used.

FIGS. 4A and 4B illustrate versions of time-control routines where a sensor may be used to indicate a use of the aerosolization device 100. For example, the sensor may comprise a switch on the housing or a contact detector on the abutment 165 or may comprise another type of movement detector that senses actuation of the aerosolization apparatus 100. Alternatively, the sensor may detect pressure and/or flow in or near the mouthpiece 120 and a particular sensed condition may be used to indicate to the controller 155 that the apparatus has been used. Alternatively, the sensor 275 may detect the engagement of lips or nostrils on the mouthpiece 120 or may detect a condition indicating that the reservoir has released the pharmaceutical formulation. In the version of FIG. 4A, the contact member 145 is moved to the first position 310 to allow a user to actuate the apparatus to provide an aerosolized pharmaceutical formulation. In response to a signal from the sensor 311, the controller 155 causes the contact member 145 to move to the second position and initiates a timer 312. Then, after the second predetermined time period has elapsed 313, the contact member 145 is again moved to the first position, and optionally an indication of the actuatability is provided to the user. The predetermined time period may be similar to the second time period in the versions of FIGS. 3A and 3B. The version of FIG. 4B is similar to the version of FIG. 4B in that steps 320, 321, 324, 325, and 326 are substantially the same as steps 300, 301, 303, 304, and 305, respectively, but with sensing and timer initiation steps 322 and 323 replacing step 302.

In another version, the controller 155 may move the contact member 145 to the first position in response to another detected condition, such as pressure. Accordingly, in this version, the sensor may comprise a pressure sensor. The sensor may be positioned in or near the mouthpiece 120 and may generate a signal related to the pressure in or near the mouthpiece 120 or other section of the housing 115. In some situations it may be desirable to assure that there will be sufficient flow through the housing 115 during use to sufficiently aerosolize the pharmaceutical formulation and/or to sufficiently deliver the aerosolized pharmaceutical formulation to the deep lungs, as discussed for example in pending U.S. patent application Ser. No. 09/583,312, filed on May 30, 2000, and entitled "Systems and Methods for Aerosolizing Pharmaceutical Formulations" and in PCT Publication WO 01/00263, both of which are incorporated herein by reference in their entireties. Thus, in a version of the invention illustrated in the flow chart of FIG. 5, the sensor may be used to control the operation of the apparatus to allow operation of the aerosolization apparatus 100 when a sufficient vacuum or flow exists in or near the mouthpiece 120. In this version, the user engages the mouthpiece 120, or a nosepiece or the like, and begins to inhale 330 with the contact member 145 in the second position. The sensor senses the pressure and/or flow in the airway caused by the inhalation 331. When the inhalation results in the pressure in the airway dropping below a threshold level 332, the controller 155 causes the contact member 145 to move to the first position. If the pressure is not below the threshold pressure, the user continues to inhale 334 and continues to generate a vacuum. The resulting flow of air delivers the aerosolized pharmaceutical formulation 335 to the deep lungs 336 of the user. In one particular version, the threshold pressure may be selected to be from about 10 $cmH_2O$ to about 50 $cmH_2O$, more preferably from about 20 $cmH_2O$ to about 40 $cmH_2O$, and most preferably about 35 $cmH_2O$. In another version, the threshold pressure is most preferably about 28 $cmH_2O$.

The controller 155 may control the operation of the aerosolization device 100 as discussed above. Although the controller 155 has been illustrated by way of an exemplary single controller device to simplify the description of present invention, it should be understood that the controller 155 may be a plurality of controller devices that may be connected to one another or a plurality of controller devices that may be connected to different components of the aerosolization device 100.

In one embodiment, the controller 155 comprises electronic hardware including electrical circuitry comprising integrated circuits that is suitable for operating or controlling the aerosolization device 100. Generally, the controller 155 is adapted to accept data input, run algorithms, produce useful output signals, and may also be used to detect data signals from the sensor and other device components, and to monitor or control the process in the aerosolization device 100. However, the controller 155 may merely perform one of these tasks. In one version, the controller 155 may comprise one or more of (i) a computer comprising a central processor unit (CPU) which is interconnected to a memory system with peripheral control components, (ii) application specific integrated circuits (ASICs) that operate particular components of the aerosolization device 100 or operate a particular process, and (iii) one or more controller interface boards along with suitable support circuitry. Typical CPUs include the PowerPC™, Pentium™, and other such processors. The ASICs are designed and preprogrammed for particular tasks, such as retrieval of data and other information from the aerosolization device 100 and/or operation of particular device components. Typical support circuitry includes for example, coprocessors, clock circuits, cache, power supplies and other well known components that are in communication with the CPU. For example, the CPU often operates in conjunction with a random access memory (RAM), a read-only memory (ROM) and other storage devices well known in the art. The RAM can be used to store the software implementation of the present invention during process implementation. The programs and subroutines of the present invention are typically stored in mass storage devices and are recalled for temporary storage in RAM when being executed by the CPU.

The software implementation and computer program code product of the present invention may be stored in a memory device, such as an EPROM, and called into RAM during execution by the controller 155. The computer program code may be written in conventional computer readable programming languages, such as for example, assembly language, C, C", Pascal, or native assembly. Suitable program code is entered into a single file, or multiple files, using a conventional text editor and stored or embodied in a computer-usable medium, such as a memory of the computer system. If the entered code text is in a high level language, the code is compiled to a compiler code which is linked with an object code of precompiled windows library routines. To execute the linked and compiled object code, the system user invokes the object code, causing the computer system to load the code in memory to perform the tasks identified in the computer program. The controller 155 and program code described herein should not be limited to the specific embodiment of the program codes described herein or housed as shown herein, and other sets of program code or computer instructions that perform equivalent functions, such as the functions described in connection with the flow charts of FIGS. 3-5, are within the scope of the present invention.

In one version, the controller 155 may comprise a microprocessor or ASIC of sufficiently small size and power consumption to be housed on or in the aerosolization device 100. For example, suitable microprocessors for use as a local microprocessor include the MC68HC711E9 by Motorola, the PIC16C74 by Microchip, and the 82930AX by Intel Corporation.

The microprocessor can include one microprocessor chip, multiple processors and/or co-processor chips, and/or digital signal processor (DSP) capability. In addition, a power supply, such as a battery, to supply power to the processor and/or to an actuator for moving the bearngin member 145 may be housed in or on the aerosolization device 100. Optionally, the battery may be rechargeable and the aerosolization device 100 may be positionable in a charging cradle when not in use.

Figure 6B:
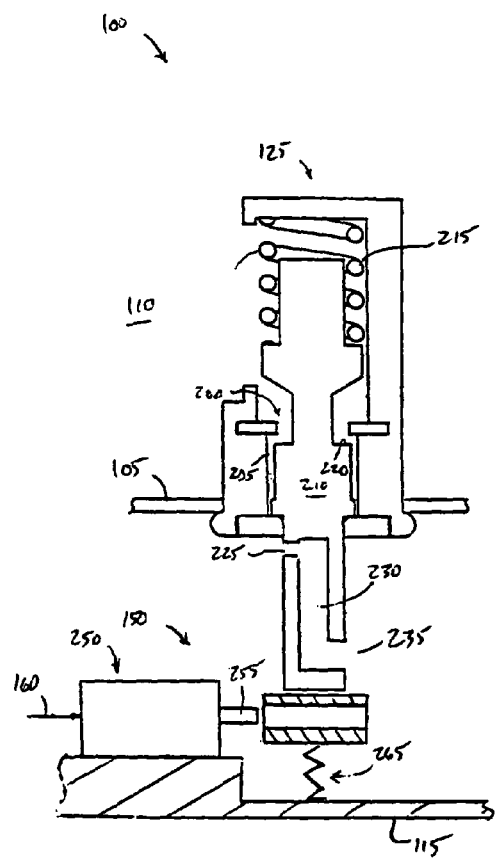

A specific version of a portion of an aerosolization apparatus 100 is shown schematically in FIGS. 6A and 6B. FIGS. 6A and 6B show the metering valve 125 in its filling position. The pharmaceutical formulation in the reservoir 110 flows through an opening 200 into a metering chamber 205. When in the filling position, the pressure in the metering chamber 205 is the same as the pressure in the reservoir 110. The metering valve 125 comprises a moveable stem 210. The stem 210 is biased into the extended position shown in FIGS. 6A and 6B by a spring 215. Movement of the stem 210 to compress the spring 215 causes actuation of the aerosolization device 100 which results in aerosolization of the pharmaceutical formulation contained within the metering chamber 130. This movement of the stem 210 causes the metered amount of the pharmaceutical formulation to be contained within the metering chamber 205 by causing a portion 220 of the stem 210 to block the opening 220 into the metering chamber 205. Simultaneously or shortly thereafter upon continued movement of the stem 210, an opening 225 into an expansion chamber 230 is caused to be in communication with the metering chamber 205. The metered amount of the pharmaceutical formulation is ejected from the metering chamber 205 into the interior of the expansion chamber 230 under the pressure of the flashing liquid propellant. As the propellant boils, vapor is generated to fill the void left in the metering chamber 205. In the expansion chamber 230 the pharmaceutical formulation undergoes expansion and further boiling. As a result, the metered amount of pharmaceutical formulation is discharged through a spray orifice 235 as an aerosolized pharmaceutical formulation. After actuation and aerosolization, the spring 215 returns the stem 210 to the position shown in FIGS. 6A and 6B and as the pressure in the metering chamber 205 and in the reservoir once again equilibrate.

Another version of an actuation controlling mechanism 150 in which the controller controls a condition of the contact member other than position is shown schematically in FIGS. 6A and 6B. In this version, a controlling signal 160 from a controller causes a change in configuration of the contact member 145 rather than a change in position. FIG. 6A shows the actuation controlling mechanism 150 in a first condition and FIG. 6B shows the actuation controlling mechanism 150 in a second condition. The aerosolization apparatus 100 may be actuated when in the first condition and may not be actuated when in the second condition. For example, in the version shown, a linear actuator, such as a solenoid 250 includes an arm 255 that is linearly extendable under the control of the controller 155. In an extended position, the arm 255 extends through an opening 260 in the contact member 145 to rigidly secure the contact member 145. In this way, the stem 210 of the metering valve 125 may bear against the rigid contact member 145 to be compressed into the container 105 to cause actuation as discussed above. In a retracted position, the arm 255 does not extend into the contact member 145, and the contact member 145 is not rigid. Accordingly, when the stem 210 is pressed downwardly, it does not move into the container 105 and there is no actuation. A biasing member, such as a spring 165 may be provided to maintain the contact member 145 in contact with the stem 210 even when in the second condition. The first condition and the second condition may be used to control the operation of the aerosolization apparatus 100 in similar manner as the first position and the second position discussed above in connection with the version of FIGS. 1A, 1B, 2A, and 2B and in connection with the flow charts of FIGS. 3 through 5.

The actuation controlling mechanism 150 of the version of FIGS. 6A and 6B offers several advantages. For example, the force required to effect the enabling of the apparatus is minimal and the enabling need only occur as the stem 210 is depressed. Thus, minimal electrical energy is necessary. In addition, the primary failure mode is a mode where the arm 255 does not extend. Accordingly, the primary failure mode presents an inactive condition.

In alternative versions, the version of FIGS. 1A through 2B or the version of FIGS. 6A and 6B may be altered so that the contact member 145 selectively contacts the top surface 140 of the container 105 and so that the force 135 is applied from the bottom of the housing 115. When the contact member 145 is not in its first position or its first configuration, then the force 135 would merely serve to move both the container 105 and the metering valve 125 upwardly. However, when the contact member is in its first position or its first configuration, then the movement of the container 105 would be restricted and the force 135 would urge the metering valve 125 into the container 105 to cause actuation of the device.

The reservoir 110 may be in a cannister in which a pharmaceutical formulation is stored in or with a propellant, such as a hydrofluoroalkane, as discussed in U.S. Pat. No. 6,309,623 and in U.S. Pat. No. 5,655,520, both of which are incorporated herein by reference in their entireties. Propellant based metered dose inhalers may employ a dry powdered pharmaceutical formulation which is suspended in a liquefied gas propellant. After actuation, the propellant evaporates almost immediately leaving a fine dry powder.

In a preferred version, the invention provides a system and method for aerosolizing a pharmaceutical formulation and delivering the pharmaceutical formulation to the lungs of the user. The pharmaceutical formulation may comprise powdered medicaments, liquid solutions or suspensions, and the like, and may include an active agent.

The active agent described herein includes an agent, drug, compound, composition of matter or mixture thereof which provides some pharmacologic, often beneficial, effect. This includes foods, food supplements, nutrients, drugs, vaccines, vitamins, and other beneficial agents. As used herein, the terms further include any physiologically or pharmacologically active substance that produces a localized or systemic effect in a patient. An active agent for incorporation in the pharmaceutical formulation described herein may be an inorganic or an organic compound, including, without limitation, drugs which act on: the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system, and the central nervous system. Suitable active agents may be selected from, for example, hypnotics and sedatives, psychic energizers, tranquilizers, respiratory drugs, anticonvulsants, muscle relaxants, antiparkinson agents (dopamine antagonists), analgesics, anti-inflammatories, antianxiety drugs (anxiolytics), appetite suppressants, antimigraine agents, muscle contractants, anti-infectives (antibiotics, antivirals, antifungals, vaccines) antiarthritics, antimalarials, antiemetics, anepileptics, bronchodilators, cytokines, growth factors, anti-cancer agents, antithrombotic agents, antihypertensives, cardiovascular drugs, antiarrhythmics, antioxicants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents. The active agent, when administered by inhalation, may act locally or systemically.

The active agent may fall into one of a number of structural classes, including but not limited to small molecules, peptides, polypeptides, proteins, polysaccharides, steroids, proteins capable of eliciting physiological effects, nucleotides, oligonucleotides, polynucleotides, fats, electrolytes, and the like.

Examples of active agents suitable for use in this invention include but are not limited to one or more of calcitonin, erythropoietin (EPO), Factor VIII, Factor IX, ceredase, cerezyme, cyclosporin, granulocyte colony stimulating factor (GCSF), thrombopoietin (TPO), alpha-1 proteinase inhibitor, elcatonin, granulocyte macrophage colony stimulating factor (GMCSF), growth hormone, human growth hormone (HGH), growth hormone releasing hormone (GHRH), heparin, low molecular weight heparin (LMWH), interferon alpha, interferon beta, interferon gamma, interleukin-1 receptor, interleukin-2, interleukin-1 receptor antagonist, interleukin-3, interleukin-4, interleukin-6, luteinizing hormone releasing hormone (LHRH), factor IX, insulin, pro-insulin, insulin analogues (e.g., mono-acylated insulin as described in U.S. Pat. No. 5,922,675, which is incorporated herein by reference in its entirety), amylin, C-peptide, somatostatin, somatostatin analogs including octreotide, vasopressin, follicle stimulating hormone (FSH), insulin-like growth factor (IGF), insulintropin, macrophage colony stimulating factor (M-CSF), nerve growth factor (NGF), tissue growth factors, keratinocyte growth factor (KGF), glial growth factor (GGF), tumor necrosis factor (TNF), endothelial growth factors, parathyroid hormone (PTH), glucagon-like peptide thymosin alpha 1, IIb/IIIa inhibitor, alpha-1 antitrypsin, phosphodiesterase (PDE) compounds, VLA-4 inhibitors, bisphosponates, respiratory syncytial virus antibody, cystic fibrosis transmembrane regulator (CFTR) gene, deoxyreibonuclease (Dnase), bactericidal/permeability increasing protein (BPI), anti-CMV antibody, 13-cis retinoic acid, macrolides such as erythromycin, oleandomycin, troleandomycin, roxithromycin, clarithromycin, davercin, azithromycin, flurithromycin, dirithromycin, josamycin, spiromycin, midecamycin, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin, aminoglycosides such as gentamicin, netilmicin, paramecin, tobramycin, amikacin, kanamycin, neomycin, and streptomycin, vancomycin, teicoplanin, rampolanin, mideplanin, colistin, daptomycin, gramicidin, colistimethate, polymixins such as polymixin B, capreomycin, bacitracin, penems; penicillins including penicllinase-sensitive agents like penicillin G, penicillin V, penicillinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefinetazole, ceftazidime, loracarbef, and moxalactam, monobactams like aztreonam; and carbapenems such as imipenem, meropenem, pentamidine isethiouate, albuterol sulfate, lidocaine, metaproterenol sulfate, beclomethasone diprepionate, triamcinolone acetamide, budesonide acetonide, fluticasone, ipratropium bromide, flunisolide, cromolyn sodium, ergotamine tartrate and where applicable, analogues, agonists, antagonists, inhibitors, and pharmaceutically acceptable salt forms of the above. In reference to peptides and proteins, the invention is intended to encompass synthetic, native, glycosylated, unglycosylated, pegylated forms, and biologically active fragments and analogs thereof.

Active agents for use in the invention further include nucleic acids, as bare nucleic acid molecules, vectors, associated viral particles, plasmid DNA or RNA or other nucleic acid constructions of a type suitable for transfection or transformation of cells, i.e., suitable for gene therapy including antisense. Further, an active agent may comprise live attenuated or killed viruses suitable for use as vaccines. Other useful drugs include those listed within the Physician's Desk Reference (most recent edition).

The amount of active agent in the pharmaceutical formulation will be that amount necessary to deliver a therapeutically effective amount of the active agent per unit dose to achieve the desired result. In practice, this will vary widely depending upon the particular agent, its activity, the severity of the condition to be treated, the patient population, dosing requirements, and the desired therapeutic effect. The composition will generally contain anywhere from about 1% by weight to about 99% by weight active agent, typically from about 2% to about 95% by weight active agent, and more typically from about 5% to 85% by weight active agent, and will also depend upon the relative amounts of additives contained in the composition. The compositions of the invention are particularly useful for active agents that are delivered in doses of from 0.001 mg/day to 100 mg/day, preferably in doses from 0.01 mg/day to 75 mg/day, and more preferably in doses from 0.10 mg/day to 50 mg/day. It is to be understood that more than one active agent may be incorporated into the formulations described herein and that the use of the term "agent" in no way excludes the use of two or more such agents.

The pharmaceutical formulation may comprise a pharmaceutically acceptable excipient or carrier which may be taken into the lungs with no significant adverse toxicological effects to the subject, and particularly to the lungs of the subject. In addition to the active agent, a pharmaceutical formulation may optionally include one or more pharmaceutical excipients which are suitable for pulmonary administration. These excipients, if present, are generally present in the composition in amounts ranging from about 0.01% to about 95% percent by weight, preferably from about 0.5 to about 80%, and more preferably from about 1 to about 60% by weight. Preferably, such excipients will, in part, serve to further improve the features of the active agent composition, for example by providing more efficient and reproducible delivery of the active agent, improving the handling characteristics of powders, such as flowability and consistency, and/or facilitating manufacturing and filling of unit dosage forms. In particular, excipient materials can often function to further improve the physical and chemical stability of the active agent, minimize the residual moisture content and hinder moisture uptake, and to enhance particle size, degree of aggregation, particle surface properties, such as rugosity, ease of inhalation, and the targeting of particles to the lung. One or more excipients may also be provided to serve as bulking agents when it is desired to reduce the concentration of active agent in the formulation.

Pharmaceutical excipients and additives useful in the present pharmaceutical formulation include but are not limited to amino acids, peptides, proteins, non-biological polymers, biological polymers, carbohydrates, such as sugars, derivatized sugars such as alditols, aldonic acids, esterified sugars, and sugar polymers, which may be present singly or in combination. Suitable excipients are those provided in WO 96/32096, which is incorporated herein by reference in its entirety. The excipient may have a glass transition temperatures (Tg) above about 35° C., preferably above about 40° C., more preferably above 45° C., most preferably above about 55° C.

Exemplary protein excipients include albumins such as human serum albumin (HSA), recombinant human albumin (rHA), gelatin, casein, hemoglobin, and the like. Suitable amino acids (outside of the dileucyl-peptides of the invention), which may also function in a buffering capacity, include alanine, glycine, arginine, betaine, histidine, glutamic acid, aspartic acid, cysteine, lysine, leucine, isoleucine, valine, methionine, phenylalanine, aspartame, tyrosine, tryptophan, and the like. Preferred are amino acids and polypeptides that function as dispersing agents. Amino acids falling into this category include hydrophobic amino acids such as leucine, valine, isoleucine, tryptophan, alanine, methionine, phenylalanine, tyrosine, histidine, and proline. Dispersibility-enhancing peptide excipients include dimers, trimers, tetramers, and pentamers comprising one or more hydrophobic amino acid components such as those described above.

Carbohydrate excipients suitable for use in the invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), pyranosyl sorbitol, myoinositol and the like.

The pharmaceutical formulation may also include a buffer or a pH adjusting agent, typically a salt prepared from an organic acid or base. Representative buffers include organic acid salts of citric acid, ascorbic acid, gluconic acid, carbonic acid, tartaric acid, succinic acid, acetic acid, or phthalic acid, Tris, tromethamine hydrochloride, or phosphate buffers.

The pharmaceutical formulation may also include polymeric excipients/additives, e.g., polyvinylpyrrolidones, derivatized celluloses such as hydroxymethylcellulose, hydroxyethylcellulose, and hydroxypropylmethylcellulose, Ficolls (a polymeric sugar), hydroxyethylstarch, dextrates (e.g., cyclodextrins, such as 2-hydroxypropyl-β-cyclodextrin and sulfobutylether-β-cyclodextrin), polyethylene glycols, and pectin.

The pharmaceutical formulation may further include flavoring agents, taste-masking agents, inorganic salts (for example sodium chloride), antimicrobial agents (for example benzalkonium chloride), sweeteners, antioxidants, antistatic agents, surfactants (for example polysorbates such as "TWEEN 20" and "TWEEN 80"), sorbitan esters, lipids (for example phospholipids such as lecithin and other phosphatidylcholines, phosphatidylethanolamines), fatty acids and fatty esters, steroids (for example cholesterol), and chelating agents (for example EDTA, zinc and other such suitable cations). Other pharmaceutical excipients and/or additives suitable for use in the compositions according to the invention are listed in "Remington: The Science & Practice of Pharmacy", $19^{th}$ ed., Williams & Williams, (1995), and in the "Physician's Desk Reference", $52^{nd}$ ed., Medical Economics, Montvale, N.J. (1998), both of which are incorporated herein by reference in their entireties.

The pharmaceutical formulation may also be treated so that it has high stability. Several attempts have dealt with improving suspension stability by increasing the solubility of surface-active agents in the HFA propellants. To this end U.S. Pat. No. 5,118,494, WO 91/11173 and WO 92/00107 disclose the use of HFA soluble fluorinated surfactants to improve suspension stability. Mixtures of HFA propellants with other perfluorinated cosolvents have also been disclosed as in WO 91/04011. Other attempts at stabilization involved the inclusion of nonfluorinated surfactants. In this respect, U.S. Pat. No. 5,492,688 discloses that some hydrophilic surfactants (with a hydrophilic/lipophilic balance greater than or equal to 9.6) have sufficient solubility in HFAs to stabilize medicament suspensions. Increases in the solubility of conventional nonfluorinated MDI surfactants (e.g. oleic acid, lecithin) can also reportedly be achieved with the use of co-solvents such as alcohols, as set forth in U.S. Pat. Nos. 5,683,677 and 5,605,674, as well as in WO 95/17195. Unfortunately, as with the prior art cosolvent systems previously discussed, merely increasing the repulsion between particles has not proved to be a very effective stabilizing mechanism in nonaqueous dispersions, such as MDI preparations. All of the aforementioned references being incorporated herein by reference in their entireties.

"Mass median diameter" or "MMD" is a measure of mean particle size, since the powders of the invention are generally polydisperse (i.e., consist of a range of particle sizes). MMD values as reported herein are determined by centrifugal sedimentation, although any number of commonly employed techniques can be used for measuring mean particle size. "Mass median aerodynamic diameter" or "MMAD" is a measure of the aerodynamic size of a dispersed particle. The aerodynamic diameter is used to describe an aerosolized powder in terms of its settling behavior, and is the diameter of a unit density sphere having the same settling velocity, generally in air, as the particle. The aerodynamic diameter encompasses particle shape, density and physical size of a particle. As used herein, MMAD refers to the midpoint or median of the aerodynamic particle size distribution of an aerosolized powder determined by cascade impaction.

In one version, the powdered formulation for use in the present invention includes a powder having a particle size selected to permit penetration into the alveoli of the lungs, that is, preferably 10 μm mass median diameter (MMD), preferably less than 7.5 μm, and most preferably less than 5 μm, and usually being in the range of 0.1 μm to 5 μm in diameter. The delivered dose efficiency (DDE) of these powders may be greater than 30%, more preferably greater than 40%, more preferably greater than 50% and most preferably greater than 60% and the aerosol particle size distribution is about 1.0-5.0 μm mass median aerodynamic diameter (MMAD), usually 1.5-4.5 μm MMAD and preferably 1.5-4.0 μm MMAD. These dry powders have a moisture content below about 10% by weight, usually below about 5% by weight, and preferably below about 3% by weight. Such powders are described in WO 95/24183, WO 96/32149, WO 99/16419, and WO 99/16422, all of which are all incorporated herein by reference in their entireties.

Although the present invention has been described in considerable detail with regard to certain preferred versions thereof, other versions are possible, and alterations, permutations and equivalents of the version shown will become apparent to those skilled in the art upon a reading of the specification and study of the drawings. For example, the relative positions of the elements in the aerosolization device may be changed, and flexible parts may be replaced by more rigid parts that are hinged, or otherwise movable, to mimic the action of the flexible part. In addition, the passageways need not necessarily be substantially linear, as shown in the drawings, but may be curved or angled, for example. Also, the various features of the versions herein can be combined in various ways to provide additional versions of the present invention. Furthermore, certain terminology has been used for the purposes of descriptive clarity, and not to limit the present invention. Therefore, any appended claims should not be limited to the description of the preferred versions contained herein and should include all such alterations, permutations, and equivalents as fall within the true spirit and scope of the present invention.

What is claimed is:

1. An aerosolization device comprising:
   a housing;
   a container comprising a reservoir storing a pharmaceutical formulation which comprises a propellant;
   a metering valve in communication with the reservoir, the metering valve being moveable into the container to an actuated position when a user applies a force to the container to cause the container to move within the housing, wherein a predetermined amount of the pharmaceutical formulation is released when the metering valve is moved to the actuated position; and
   a contact member in the housing, the contact member being moveable between a first position and a second position, wherein a portion of the metering valve is able to contact the contact member when in the first position and is unable to contact the contact member when in the second position.

2. An aerosolization device according to claim 1 wherein the metering valve may be moved to the actuated position only when the contact member is in the first position.

3. An aerosolization device according to claim 1 wherein the container and the metering valve are moveable within the housing and wherein when the contact member is in the first position, the metering valve is able to contact the contact member so that is may be moved into the container to the actuated position and when the contact member is in the second position, the metering valve is unable to contact the contact member and cannot be moved into the container to the actuated position.

4. An aerosolization device according to claim 1 further comprising a controller adapted to selectively control the movement of the contact member.

5. An aerosolization device according to claim 1 wherein the container moves within the housing when a force is applied by the user directly to a surface of the container.

6. An aerosolization device according to claim 1 wherein the container moves within the housing when a force is applied to an intermediate member.

7. An aerosolization device comprising:
   a housing;
   a container comprising a reservoir storing a pharmaceutical formulation which comprises a propellant;
   a metering valve in communication with the reservoir, the metering valve being moveable into the container to an actuated position when a user applies a force to the container to cause the container to move within the housing, wherein a predetermined amount of the pharmaceutical formulation is released when the metering valve is moved to the actuated position; and
   a contact member in the housing, the contact member having a first configuration and a second configuration, wherein a portion of the metering valve is able to contact the contact member when in the first configuration in a manner which allows the metering valve to be moved to the actuated position, and wherein a portion of the metering valve is able to contact the contact member when in the second configuration in a manner which does not allow the metering valve to be moved to the actuated position.

8. An aerosolization device according to claim 7 wherein the metering valve may be moved to the actuated position only when the contact member is in the first configuration.

9. An aerosolization device according to claim 7 wherein the container and the metering valve are moveable within the housing and wherein when the contact member is in the first configuration, the metering valve is able to contact the contact member so that is may be moved into the container to the actuated position and when the contact member is in the second position, the metering valve is able to contact the contact member but cannot be moved into the container to the actuated position.

10. An aerosolization device according to claim 7 wherein the contact member is rigid in the first configuration and is flexible in the second configuration.

11. An aerosolization device according to claim 7 further comprising a controller adapted to selectively control the configuration of the contact member.

12. An aerosolization device comprising:
    a housing;
    a container comprising a reservoir storing a pharmaceutical formulation which comprises a propellant;
    a metering valve in communication with the reservoir, the metering valve being moveable into the container to an actuated position when a user applies a force to the container to cause the container to move within the housing, wherein a predetermined amount of the pharmaceutical formulation is released when the metering valve is moved to the actuated position; and
    a contact member in the housing, the contact member being moveable from a first condition to a second condition, wherein when the contact member is in the first condition, the metering valve may contact the contact member so as to allow the metering valve to be moved to the actuated position, and wherein a portion of the metering valve is able to contact the contact member when in the second condition in a manner which does not allow the metering valve to be moved to the actuated position.

13. An aerosolization device according to claim 12 wherein the first condition is a first position and wherein the second condition is a second position.

14. An aerosolization device according to claim 13 wherein first position is a position in the housing where the contact member may contact a portion of the metering valve.

15. An aerosolization device according to claim 12 wherein the first condition is a first configuration and wherein the second condition is a second configuration, and wherein the first configuration is a rigid configuration.

16. An aerosolization device according to claim 15 wherein the second configuration is a relatively flexible configuration.

17. An aerosolization device according to claim 12 wherein the metering valve may be moved to the actuated position only when the contact member is in the first condition.

18. An aerosolization device according to claim 12 wherein the container and the metering valve are moveable within the housing and wherein when the contact member is in the first condition, the metering valve is able to contact the contact member so that is may be moved into the container to the actuated position and when the contact member is in the second condition, the metering valve cannot be moved into the container to the actuated position.

19. An aerosolization device according to claim 12 further comprising a controller adapted to selectively control the condition of the contact member.

20. An aerosolization device comprising:
    a housing;
    a container comprising a reservoir storing a pharmaceutical formulation which comprises a propellant;
    a metering valve in communication with the reservoir, the metering valve being moveable into the container to an actuated position when a user applies a force to the container to cause the container to move within the housing, wherein a predetermined amount of the pharmaceutical formulation is released when the metering valve is moved to the actuated position; and
    a contact member in the housing,
    wherein the metering valve may be moved to the actuated position when the metering valve and/or the container is able to contact the contact member and may not be actuated when the metering valve and/or the container is unable to contact the contact member.

21. An aerosolization device according to claim 20 further comprising a controller adapted to selectively control when the metering valve may and may not be moved to the actuated position.

22. An aerosolization device comprising:
    a housing;
    a container comprising a reservoir storing a pharmaceutical formulation which comprises a propellant;
    a metering valve in communication with the reservoir, the metering valve being moveable into the container to an actuated position when a user applies a force to the container to cause the container to move within the housing, wherein a predetermined amount of the pharmaceutical formulation is released when the metering valve is moved to the actuated position; and a contact member in the housing, wherein the metering valve may be moved to the actuated position when the metering valve and/or the container is able to contact the contact member in a rigid configuration and may not be actuated when the metering valve and/or the container is unable to contact the contact member in a rigid configuration.

23. An aerosolization device according to claim 22 further comprising a controller adapted to selectively control when the metering valve may and may not be moved to the actuated position.

24. A method of controlling the operation of an aerosolization device, the aerosolization device comprising a container comprising a reservoir storing a pharmaceutical formulation which comprises a propellant, and the aerosolization device comprising a metering valve in communication with the reservoir, the metering valve being moveable into the container to an actuated position when a user applies a force to the container to cause the container to move, wherein a predetermined amount of the pharmaceutical formulation is released when the metering valve is moved to the actuated position, the method comprising:

positioning a contact member in a first position where the contact member may contact the metering valve and/or the container to allow the metering valve to be moved to the actuated position; and positioning the contact member in a second position where the metering valve may not be moved to the actuated position.

25. A method according to claim 24 wherein the second position is a position where the contact member may not be contacted by the metering valve or the container.

26. A method according to claim 24 comprising returning the contact member to the first position after a condition is met.

27. A method according to claim 26 wherein the condition is the passage of a predetermined amount of time.

28. A method of controlling the operation of an aerosolization device, the aerosolization device comprising a container comprising a reservoir storing a pharmaceutical formulation which comprises a propellant, and the aerosolization device comprising a metering valve in communication with the reservoir, the metering valve being moveable into the container to an actuated position when a user applies a force to the container to cause the container to move, wherein a predetermined amount of the pharmaceutical formulation is released when the metering valve is moved to the actuated position, the method comprising:

configuring a contact member in a first configuration wherein the contact member may contact the metering valve to allow the metering valve to be moved to the actuated position; and configuring the contact member in a second configuration wherein the metering valve may contact the contact member but may not be moved to the actuated position.

29. A method according to claim 28 wherein the first configuration is a rigid configuration.

30. A method according to claim 28 wherein the second configuration is a flexible configuration.

31. A method according to claim 28 comprising returning the contact member to the first configuration after a condition is met.

32. A method according to claim 31 wherein the condition is the passage of a predetermined amount of time.

* * * * *